United States Patent [19]
Koike et al.

[11] Patent Number: 5,157,165
[45] Date of Patent: Oct. 20, 1992

[54] METHOD FOR PREPARING HIGHLY PURE 1,1,2,2-TETRAKIS(4-HYDROXY-3,5-DIMETHYLPHENYL)ETHANE

[75] Inventors: Naru Koike; Shigeru Iimuro; Mizuo Ito, all of Aichi, Japan

[73] Assignee: Mitsui Toatsu Chemicals, Inc., Tokyo, Japan

[21] Appl. No.: 796,440

[22] Filed: Nov. 22, 1991

[30] Foreign Application Priority Data

Nov. 26, 1990 [JP] Japan ................... 2-317846

[51] Int. Cl.$^5$ ............................................ C07C 39/16
[52] U.S. Cl. ................................... 568/723; 568/720; 528/219; 528/98
[58] Field of Search ................. 528/98, 219; 568/720, 568/723

[56] References Cited

U.S. PATENT DOCUMENTS

| | | | |
|---|---|---|---|
| 2,779,800 | 1/1957 | Holm et al. | 528/98 |
| 3,013,087 | 12/1961 | Schwarzer | 528/98 |
| 3,092,610 | 6/1963 | Schwarzer | 528/98 |
| 3,218,370 | 11/1965 | Fry et al. | 525/485 |
| 3,245,865 | 4/1966 | Hawkins et al. | 428/417 |
| 3,390,123 | 6/1968 | Frichette | 525/534 |
| 3,452,116 | 6/1969 | Schwarzer | 528/98 |
| 3,694,407 | 9/1972 | Krikorian | 528/98 |
| 4,915,875 | 4/1990 | Diephouse et al. | 552/304 |
| 5,012,016 | 4/1991 | Li | 528/204 |

FOREIGN PATENT DOCUMENTS

| | | |
|---|---|---|
| 63-223020 | 9/1988 | Japan . |
| 64-74213 | 3/1989 | Japan . |
| 504396 | 4/1971 | Switzerland . |
| 523320 | 7/1940 | United Kingdom . |

OTHER PUBLICATIONS

Australian Journal of Chemistry, vol. 33, No. 2, Feb. 1980, "Oxidation of Bisphenols, II Some Compounds Related to Galvinoxyl", Colegate et al, pp. 351–369.

*Primary Examiner*—Melvyn I. Marquis
*Assistant Examiner*—Randy Gulakowski
*Attorney, Agent, or Firm*—Burns, Doane, Swecker & Mathis

[57] ABSTRACT

Herein provided are a method for preparing 1,1,2,2-tetrakis(4-hydroxy-3,5-dimethylphenyl)ethane (TKXE) comprising subjecting two molecules of bis(3,5-dimethyl-4-hydroxyphenyl) methane to dehydration-condensation under oxidizing conditions, an epoxy resin prepared by epoxidating TKXE obtained by the method and an epoxy resin composition comprising TKXE obtained by the method as a hardener and an epoxy resin as well as methods for preparing the resin and composition. The method makes it possible to prepare highly pure TKXE in the form of crystals. Moreover, the epoxy resin and the epoxy resin composition can provide hardened products excellent in physical properties such as heat resistance and mechanical strength.

7 Claims, 2 Drawing Sheets

METHOD FOR PREPARING HIGHLY PURE 1,1,2,2-TETRAKIS(4-HYDROXY-3,5-DIMETHYLPHENYL)ETHANE

BACKGROUND OF THE INVENTION (a) Field of the Invention

The present invention relates to a method for preparing a highly pure 1,1,2,2-tetrakis(4-hydroxy-3,5-dimethylphenyl) ethane, an epoxy resin composition comprising, as a hardener, the highly pure compound prepared by the method, an epoxy resin derived from the highly pure compound prepared by the method, and methods for preparing the epoxy resin composition and the epoxy resin.

(b) Description of the Prior Art 1,1,2,2-tetrakis(4-hydroxy-3,5-dimethylphenyl)ethane (hereinafter referred to as "tetrakisxylenolethane" or "TKXE") has been used as, for instance, a starting material for preparing phenol resins or a hardener for epoxy resins For instance, Japanese Unexamined Patent Publication (hereinafter referred to as "J. P. KOKAI") No. Sho 64-74213 discloses an epoxy resin composition comprising an epoxy compound obtained by epoxidating TKXE and TKXE, as a hardener in a specific mixing ratio in which these TKXE's are obtained by condensing 2,6-xylenol and glyoxal in the presence of an oxidizing catalyst.

Glyoxal is quite unstable in the anhydrous state and is in general put on the market in the form of an aqueous solution having a concentration ranging from 40 to 50% by weight. If such an aqueous solution of glyoxal is used as glyoxal component, the condensation of 2,6-xylenol and glyoxal is necessarily performed in the presence of water. When 2,6-xylenol and glyoxal are condensed in the presence of water, low molecular weight by-products such as glyoxal condensates are simultaneously produced in a large amount in addition to TKXE and these low molecular weight substances are very difficult to separate from TKXE. For this reason, the foregoing method cannot provide highly pure TKXE.

Accordingly, TKXE prepared by condensing 2,6-xylenol and glyoxal in the presence of an oxidizing catalyst, which contains impurities such as low molecular weight substances and which has a low purity, must be used in such a method as a starting material for preparing an epoxy resin or a hardener for epoxy resins.

If TKXE which contains low molecular weight substances such as glyoxal condensates is used as a starting material for preparing an epoxy resin or a hardener for epoxy resins, the resulting hardened product has low physical properties such as heat resistance and mechanical strength. Therefore, a problem arises when the hardened product is used in particular as a material for electric and/or electronic applications such as that for sealing IC's.

Moreover, J.P. KOKAI No. Sho 63-223020 discloses a method for preparing polyphenols which comprises condensing phenols with dialdehydes such as glyoxal and glutaraldehyde in the presence of an acid catalyst wherein the content of water in the reaction system is controlled to a level of not more than 2% by weight.

However, this method still uses dialdehydes in the form of aqueous solutions as in the foregoing methods although the water content of the reaction system is reduced to a level of not more than 2% by weight. Thus, in this method, it is required that a large amount of water contained in the reaction system is removed through, for instance, distillation prior to the condensation reaction to control the water content of the reaction system to not more than 2% by weight. These operations make the condensation reaction process complicated and require the use of excess energy for the removal of a large amount of water through, for instance, distillation. Moreover, the water removed from the reaction system contains a large amount of organic substances and, therefore, cannot be discharged out of the plant without any pretreatment. For this reason, it is required for the use of a water purifying plant such as an activated sludge processing apparatus. Furthermore, the formation of low molecular weight substances such as glyoxal condensates cannot completely be suppressed since the condensation reaction of phenols and dialdehydes is still performed in the presence of water although the content thereof is low of the order of not more than 2% by weight. Thus, this method has still been insufficient for use in the preparation of highly pure TKXE.

SUMMARY OF THE INVENTION

Accordingly, an object of the present invention is to provide a method for preparing a highly pure 1,1,2,2-tetrakis(4-hydroxy-3,5-dimethylphenyl)ethane (TKXE) which does not require the use of the foregoing complicated operations, does not accompany excessive energy consumption and does not generate a large amount of waste water containing organic substances.

Another object of the present invention is to provide an epoxy resin and an epoxy resin composition which can provide a hardened product having excellent physical properties such as heat resistance and mechanical strength as well as a method for preparing the epoxy resin and epoxy resin composition.

The inventors of this invention have conducted various studies to achieve the foregoing objects, have found out that highly pure TKXE can effectively be obtained by subjecting two molecules of bis(3,5-dimethyl-4-hydroxyphenyl)methane (hereinafter referred to as "bisxylenol F" or "BXF") to dehydration-condensation and thus have completed the present invention.

Moreover, the inventors have also found out that a hardened epoxy resin product obtained by epoxidating the highly pure TKXE thus prepared as well as that obtained by hardening an epoxy resin composition which comprises the highly pure TKXE thus obtained as a hardener exhibit excellent heat resistance and mechanical strength and thus have completed the present invention.

According to an aspect of the present invention, there is provided a method for preparing TKXE which comprises subjecting two molecules of BXF to dehydration-condensation under oxidizing conditions.

The method according to the present invention, although the prior method cannot provide TKXE in the form of crystals, makes it possible to provide highly pure TKXE in the form of crystals. If the resulting TKXE is used as a starting material for preparing an epoxy resin or a hardener for epoxy resins, it can thus provide hardened products having excellent properties such as heat resistance, mechanical strength and electrical properties and the hardened products are suitable for use in such applications as electric and/or electronic parts.

According to a second aspect of the present invention, there are provided an epoxy resin obtained by subjecting two molecules of BXF to dehydration-condensation under oxidizing conditions to give highly pure TKXE and a method for preparing an epoxy resin which comprises subjecting two molecules of BXF to dehydration-condensation under oxidizing conditions to give highly pure TKXE and then epoxidating the resulting compound with an epihalohydrin at a temperature ranging from 40° to 120° C. in the presence of a hydrogen halide acceptor.

According to a third aspect of the present invention, there are provided an epoxy resin composition comprising highly pure TKXE as a hardener, which is obtained by subjecting two molecules of BXF to dehydration-condensation under oxidizing conditions, and an epoxy resin wherein the amounts of the epoxy resin and hardener are selected so that the amount of the hydroxyl groups of the hardener ranges from 0.5 to 2 moles per mole of the epoxy groups of the epoxy resin, as well as a method for preparing an epoxy resin composition comprising preparing highly pure TKXE by subjecting two molecules of BXF to dehydration-condensation under oxidizing conditions and admixing the resulting compound and an epoxy resin in such a mixing ratio that the amount of the hydroxyl groups of the hardener ranges from 0.5 to 2 moles per mole of the epoxy groups of the epoxy resin.

BRIEF DESCRIPTION OF THE DRAWINGS

In FIG. 2, a curve A represents the NMR spectra and a curve B represents the integration curve of the NMR spectra.

DESCRIPTION OF THE PREFERRED EMBODIMENTS

Figure 1:
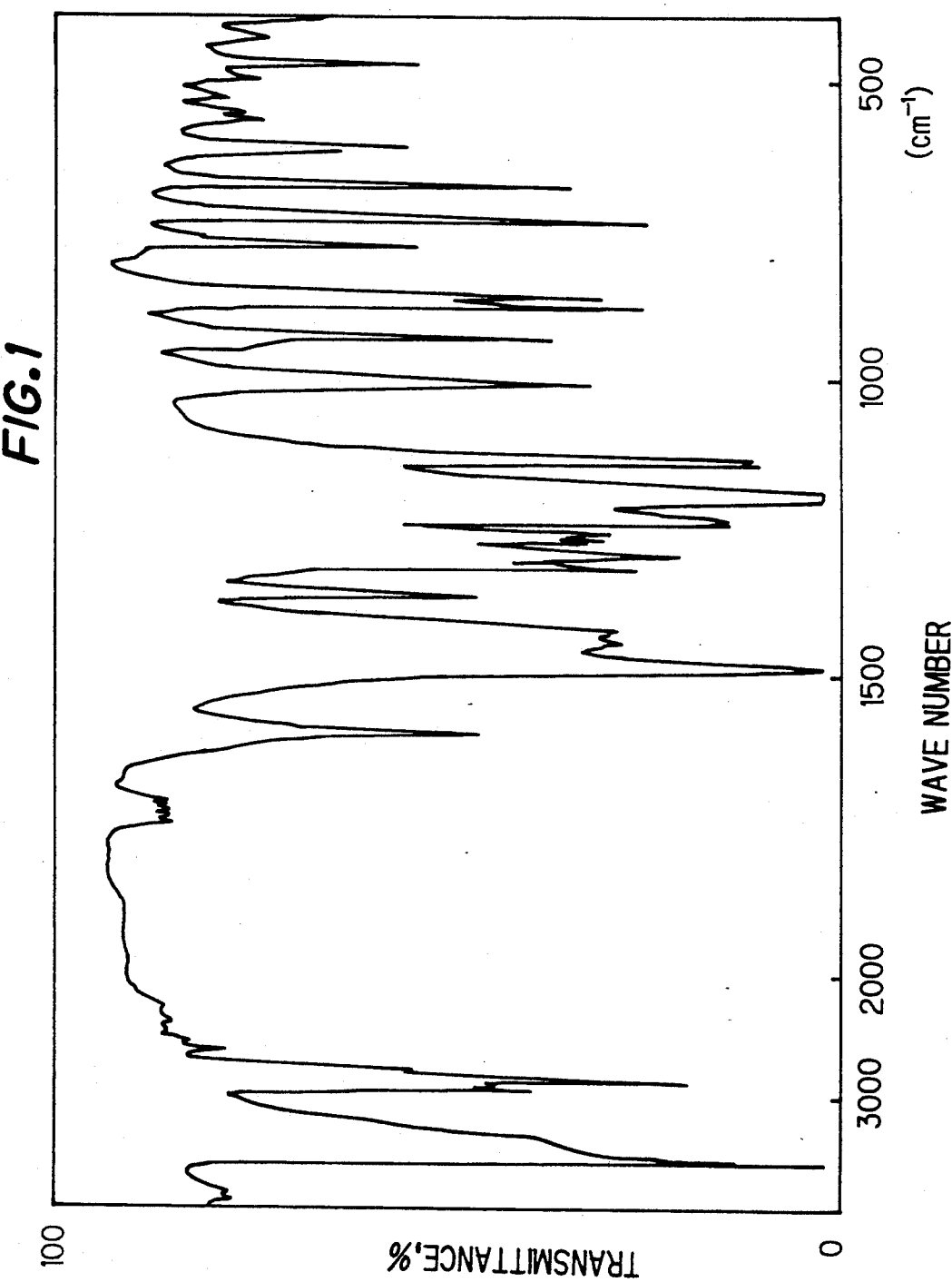
FIG. 1 shows infrared absorption spectra of TKXE obtained in Example 1.

In the method for preparing TKXE according to the present invention, two molecules of BXF represented by the following structural formula (1):

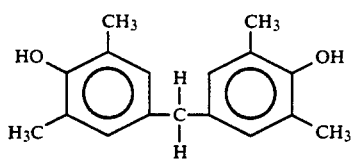

are subjected to a dehydration-condensation reaction under oxidizing conditions to give one molecule each of water and TKXE represented by the following structural formula (2):

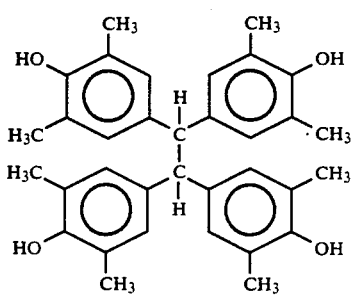

BXF used in the method of the present invention is not restricted to a specific one and those prepared by any known method can be used without any trouble. For instance, it can be obtained by condensing 2,6-xylenol and formalin at a temperature ranging from 80° to 90° C. in the presence of n-butanol and phosphoric acid as a catalyst. In this case, low molecular weight substances such as formalin condensates are simultaneously produced, but these by-products can easily be removed from TKXE together with the unreacted BXF. Therefore, highly pure TKXE can effectively be prepared according to this method.

The dehydration-condensation reaction of two BXF molecules proceeds under any condition so far as it is performed under oxidizing conditions. Thus, the reaction may be performed under press, under reduced pressure or at ordinary pressure. TKXE is preferably produced by subjecting two BXF molecules in an oxygen-containing gas atmosphere such as air or oxygen gas atmosphere. To improve the reaction rate, it is preferred to compulsorily blow air or oxygen gas through the reaction system. The amount of air to be blown through the reaction system is not restricted to a specific level and varies dependent upon various factors such as the reaction temperature and the presence or absence of a catalyst, but in general the flow rate thereof is in the order of from 10 to 1000 ml/min per 1 g of BXF. When oxygen gas is used, it is sufficient to use it in an amount of about ¼ time that of air. The air or oxygen blown through the reaction system is exhausted out of the system after passing through a post-treating device such as a reflux condenser.

According to the method of this invention, the dehydration-condensation reaction proceeds through heating of BXF in the air in the absence of any catalyst to give TKXE. Alternatively, BXF is first molten by heating and then the dehydration-condensation reaction may be performed while compulsorily blowing air or oxygen through the melt. Further, if the reaction is carried out in the presence of an oxidizing catalyst while compulsorily blowing air or oxygen through the reaction system, the reaction rate can substantially be improved.

The dehydration-condensation reaction is preferably performed at a temperature ranging from room temperature to 310° C. If the reaction is carried out in the presence of an oxidizing catalyst, it can proceeds even at a temperature lower than room temperature, but the reaction rate is too low. On the other hand, if the reaction temperature exceeds 310° C., the resulting TKXE may be decomposed.

If the dehydration-condensation reaction is performed in the absence of any catalyst, the reaction temperature preferably ranges from 150° to 310° C. This is because, if it is less than 150° C., the reaction rate is too slow. When any catalyst is not used, the dehydration-condensation reaction is most preferably carried out at a temperature ranging from 180° to 300° C. while blowing air or oxygen gas through BXF in the molten state. In this case, the resulting TKXE is precipitated out in the form of crystals. Thus, after the completion of the reaction, the resulting TKXE can be recovered in the form of the crystals thereof by simply filtering the reaction mixture while maintaining the reaction temperature. TKXE having more higher purity can be obtained if the TKXE crystals thus obtained are washed with a solvent in which TKXE is insoluble, but BXF is soluble. The dehydration-condensation reaction may likewise be performed in such a solvent by dissolving BXF in the solvent and then performing the reaction while blowing air or oxygen through the reaction solution.

If an oxidizing catalyst is used, BXF as a starting material and the oxidizing catalyst are dissolved in a solvent to give a solution and then the dehydration-condensation reaction is carried out while blowing air or oxygen through the solution. In this case, the reaction temperature preferably ranges from room temperature to 150° C.

The oxidizing catalyst is not restricted to a specific one and any catalyst currently used as an oxidizing catalyst can be used. Examples of such catalysts are metal oxides such as copper oxide, molybdenum oxide, zinc oxide, cobalt oxide and vanadium pentoxide; vanadium tetrachloride, lead chloride and lead tetraacetate.

TKXE can be obtained from BXF in the presence of an oxidizing agent such as potassium permanganate or potassium bichromate, the yield of TKXE is liable to be reduced due to the oxidation of BXF per se.

In the dehydration-condensation reaction, it is preferred that the water formed through the reaction be continuously removed and discharged out of the system through an apparatus fitted to a reactor such as a reflux condenser irrespective of the foregoing conditions.

Examples of solvents which can be used in the dehydration-condensation reaction or in the washing of the resulting TKXE include aliphatic alcohols such as methanol, ethanol, propanol, butanol, pentanol, hexanol, octanol and nonanol; aromatic alcohols such as benzyl alcohol; aromatic compounds such as benzene, toluene and xylene; ethers such as dimethyl ether, methyl ethyl ether and diethyl ether; and acetonitrile. These solvents may be used alone or in any combination thereof. Among these, preferred are those which are liquids at the reaction and/or washing temperature. The use of a solvent which is in liquid state at the reaction temperature permits the practice of the reaction at ordinary pressure.

It is sufficient to use a solvent in an amount such that the starting material, BXF, can be completely dissolved, but in general the amount (by weight) thereof desirably ranges from 1 to 10 times that of BXF used. On the other hand, the amount thereof used for washing the resulting TKXE suitably ranges from 1 to 100 times that of TKXE (by weight).

Any method for washing the resulting TKXE may be adopted. For instance, it may be extracted by means of, for instance, Soxhlet extractor or TKXE is suspended in a solvent and stirred at a temperature ranging from room temperature to the boiling point of the solvent used.

The TKXE obtained according to the method of the present invention is used as a starting material for preparing phenol and epoxy resins. Moreover, it can suitably be used as a hardener for epoxy resins.

The TKXE prepared by the present invention can be converted into an epoxy resin in the usual manner. More specifically, an epoxy resin can be obtained by epoxidating the TKXE prepared according to the present invention with an epihalohydrin, preferably epichlorohydrin at a temperature ranging from 40° to 120° C. in the presence of a hydrogen halide acceptor.

Examples of hydrogen halide acceptors include alkali metal hydroxides such as potassium hydroxide and sodium hydroxide. Preferably, the hydrogen halide acceptor is gradually added to a heated mixture of the TKXE and an epihalohydrin to thus maintain the pH of the reaction mixture at about 6.5 to 10.

In the epoxidation reaction, the epihalohydrin is used in an excess amount ranging from 2.0 to 30 equivalents, preferably 2.0 to 10 equivalents per equivalent of OH group of the TKXE. The removal of the excess acceptor and salts simultaneously formed from the reaction product is usually performed by means of, for instance, water washing.

The TKXE obtained according to the present invention can be used as a hardener for the foregoing epoxy resin and other epoxy resins.

Examples of other epoxy resins are phenolic glycidyl ether epoxy resins such as phenol-novolak, phenol-aralkyl, dicyclopentadiene-modified phenol and resolphenol epoxy resins; alcoholic glycidyl ether epoxy resins such as butanediol, polyethylene glycol and polypropylene glycol epoxy resins; glycidyl carboxylate epoxy resins such as phthalic, isophthalic, terephthalic and tetrahydrophthalic epoxy resins; epoxy resins whose active hydrogen linked to a nitrogen atom is substituted with a glycidyl group such as aniline type and isocyanuric acid type ones; and alicyclic epoxy resins obtained by epoxidating intramolecular olefins.

The amounts of the epoxy resin and the hardener, TKXE, are selected so that the amount of the phenolic hydroxyl groups ranges from 0.5 to 2 moles per mole of the epoxy group of the epoxy resin. If the amount of the phenolic hydroxyl group is less than 0.5 mole or more than 2.0 moles, the resulting hardened product has poor physical properties such as heat resistance and mechanical strength.

Moreover, the epoxy resin composition comprising the foregoing epoxy resin and the TKXE obtained according to the present invention may further comprise a hardening accelerator for the reduction of the time required for the hardening reaction between the epoxy resin and the phenolic hydroxyl groups.

Examples of such hardening accelerators include imidazoles such as 2-methylimidazole, 2-ethyl-4-methylimidazole, 2-phenylimidazole and 2-phenyl-4-methylimidazole; tertiary amines such as tris(dimethylaminomethyl)phenol, triethylenediamine and benzyldimethylamine; organic phosphines such as triphenylphosphine, tributylphosphine, tricyclohexylphosphine and methyldiphenylphosphine; and diazabicycloalkenes such as 1,8-diazabicyclo(5,4,0)undecene-7.

The amount of these hardening accelerators preferably ranges from 0.001 to 5% by weight on the basis of the weight of the epoxy resin used. If the amount thereof is beyond the range defined above, the physical properties of the resulting hardened product such as heat resistance and mechanical strength are liable to be impaired.

The epoxy resin composition of the present invention may further comprise inorganic fillers selected from the group consisting of crystalline silica, fused silica, alumina, clay, titanium white, zircon, beryllia, magnesia, zirconia, forsterite, steatite, spinel, murite, titania, barium sulfate, quartz glass, aluminum hydroxide, potassium titanate, silicon carbide, silicon nitride and glass fibers, which may be used alone or in any combination thereof.

In addition, the epoxy resin composition of the present invention may optionally comprise releasing agents such as higher fatty acids, metal salts of higher fatty acids, esters, natural waxes, synthetic waxes, acid amides and paraffins; flame retardants such as bromine atom containing compounds, antimony and phosphorus; pigments such as carbon black; silane coupling agents such as epoxysilane, aminosilane, vinylsilane, alkylsilane and organic titanates; and other additives such as agents for imparting flexibility to the resulting hardened product.

The epoxy resin composition of the present invention may be prepared in any method, but in general be prepared by a method comprising sufficiently mixing the foregoing components at a predetermined mixing ratio by, for instance, a mixer, then kneading the mixture using heated rollers or a screw extruder, cooling the kneaded product and then pulverizing the same.

The present invention will hereunder be described in more detail with reference to the following non-limitative working examples and the effects practically achieved by the present invention will also be discussed in detail in comparison with the following comparative examples.

EXAMPLE 1

To a heat-resistant glass container equipped with a stirring machine, a reflux condenser and a temperature controlling device, there were charged 2.0 g of BXF and 5.0 g of 2-ethylhexanol followed by stirring of the mixture to thus completely dissolve the BXF in the 2-ethylhexanol. The dehydration-condensation reaction was carried out at 150° C. while blowing air through the solution at a flow rate of 30 ml/min. The air blown through the reaction system was exhausted out of the system together with the water formed during the reaction through the reflux condenser. About one hour after the initiation of the reaction, crystallization of the resulting TKXE was started. The reaction was interrupted after about 6 hours.

The reaction mixture was cooled down to room temperature and filtered to recover the crystals of TKXE. The resulting TKXE crystals were introduced into 10 g of methanol, stirred at 60° C. for 5 minutes to wash the crystals and to thus remove the unreacted BXF and by-products. The crystals were filtered and dried at 100° C. for 2 hours to give 0.18 g of TKXE in the form of white crystals.

The resulting white crystals were analyzed by high performance liquid chromatography (HPLC) and the purity thereof was found to be 99.5% by weight. They were further analyzed by NMR spectroscopy and mass spectroscopy and it was confirmed that they were just TKXE.

Elemental analysis: Calculated: C 80%; H 7.5%.
Found: C 79%; H 8.0%.

Figure 2:
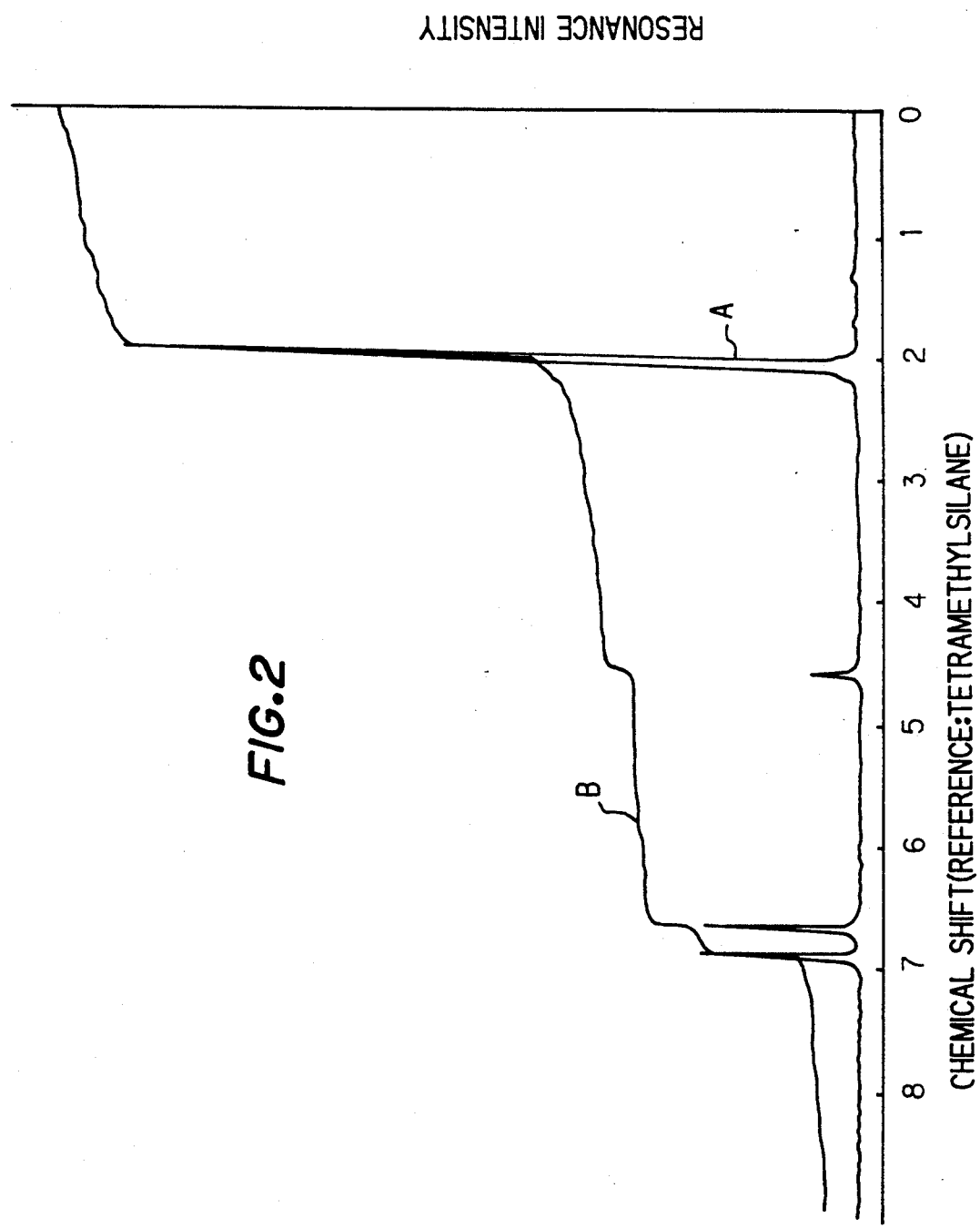
FIG. 2 shows nuclear magnetic resonance (NMR) spectra of TKXE obtained in Example 1.

Further, the decomposition temperature thereof was also determined with a thermobalance and found to be 313° C. The results of IR and NMR spectroscopic measurements of the resulting TKXE are shown in FIGS. 1 and 2 respectively. In FIG. 2, a curve A represents the NMR spectra and a curve B represents the integration curve of the NMR spectra.

EXAMPLE 2

BXF (2.0 g) was introduced into the same container used in Example 1 and then heated to 180° C. to give molten BXF. The dehydration-condensation reaction was carried out while blowing air through the molten BXF at a flow rate of 30 ml/min. The water formed during the reaction was exhausted out of the system through the reflux condenser. About one hour after the initiation of the reaction, crystallization of the resulting TKXE was started. The reaction was interrupted after about 3 hours.

The resulting reaction mixture was filtered at the reaction temperature to remove the unreacted molten BXF. The resulting TKXE crystals were cooled down to room temperature and introduced into 10 g of methanol, stirred at 60° C. for 5 minutes to wash the crystals and to remove a small amount of the unreacted BXF and by-products adhered to the crystals. The crystals were filtered and dried to give 0.18 g of TKXE as white crystals.

EXAMPLES 3 to 6

The same procedures used in Example 2 were repeated except that the conditions listed in the following Table 1 were adopted t give TKXE. The results thus obtained are summarized in Table 1.

EXAMPLE 7

The same procedures used in Example 1 were repeated except that oxygen was substituted for the air used therein to give TKXE. The results obtained are listed in Table 1.

EXAMPLES 8 to 12

The same procedures used in Example 2 were repeated except that oxygen was substituted for the air used therein to give TKXE. The results obtained are listed in Table 1.

EXAMPLE 13

There were charged 10 g of BXF, 50 g of methanol and 7.5 g of vanadium tetrachloride in the same container used in Example 1, the resulting mixture was stirred at 40° C. to give a methanolic solution. The dehydration-condensation reaction was carried out at 40° C. for 2 hours in the air. The reaction mixture was filtered to recover the resulting crystals which were then introduced into 200 g of a 1:1 (weight ratio) methanol/acetonitrile mixture and stirred at 60° C. for 5 minuted to wash the crystals. Then the crystals thus washed were recovered by filtration and dried to give 4.1 g of TKXE crystals. The results obtained are listed in Table 1.

TABLE 1

| Ex. No. | Oxygen Source | Temp.(°C.) | Purity(%) | Yield(%) |
|---|---|---|---|---|
| 1 | air | 150 | 99.5 | 9 |
| 2 | air | 180 | 99.5 | 18 |
| 3 | air | 200 | 99.6 | 37 |
| 4 | air | 220 | 99.3 | 17 |
| 5 | air | 250 | 99.5 | 7 |
| 6 | air | 300 | 99.1 | 1 |
| 7 | oxygen | 150 | 99.6 | 15 |
| 8 | oxygen | 180 | 99.6 | 30 |
| 9 | oxygen | 200 | 99.5 | 50 |
| 10 | oxygen | 220 | 99.4 | 36 |
| 11 | oxygen | 250 | 99.6 | 17 |
| 12 | oxygen | 300 | 99.2 | 5 |
| 13 | air + VCl$_4$ | 40 | 99.5 | 41 |

COMPARATIVE EXAMPLE 1

To a 100 ml flask equipped with a stirring machine, a temperature controlling device, a water separator and a dropping funnel, there were added 61 g of 2,6-xylenol and 11.5 g of a 40% aqueous solution of glyoxal and then 6 g of the water in the reaction mixture was distilled off at a temperature of 100 to 105° C. and a pressure of 700 mmHg. After the water content of the reaction system reached 1.7% by weight, a 5% aqueous solution of p-toluenesulfonic acid (1.9 g) was gradually added to the system through the dropping funnel, while the water formed during the condensation reaction was continuously distilled off to thus maintain the water content of the reaction system at 0.9 to 1.9% by weight and to proceed the condensation reaction. The reaction was conducted at 110° C. for 2 hours.

After the completion of the condensation reaction, the reaction system was neutralized by the addition of 5.4 g of a 0.4% caustic soda aqueous solution. The system was further heated to 180° C. under reduced pressure for distilling off the unreacted 2,6-xylenol, water or the like to give 29 g of a reaction product (the reaction product will hereinafter be referred to as "polyphenol").

The resulting polyphenol was analyzed by high performance liquid chromatography (HPLC) and the TKXE content (purity) of the polyphenol was found to be 51% by weight. The polyphenol comprised about 10% by weight of low molecular weight substances and about 39% by weight of highly condensed products. It was tried to perform dissolution/recrystallization of the resulting polyphenol in a tetrahydrofuran/methanol mixed system, but the separation of the impurities from TKXE was impossible or very difficult. Furthermore, the polyphenol was washed with methanol, toluene and acetonitrile, but the impurities could not be removed at all.

EXAMPLE 14

There were mixed 30 parts by weight of TKXE prepared according to the method used in Example 1, 100 parts by weight of an o-cresol/novolak epoxy resin (available from Nippon Kayaku Co., Ltd. under the trade name of EOCN-102S; epoxy equivalent 214; softening point 75° C.) and 0.5 part by weight of 2-ethyl-4-methylimidazole. The resulting mixture was kneaded at a kneading temperature of 100° to 110° C. for 5 minutes through roll kneading. The resulting sheet-like kneaded product was cooled and then pulverized to give an epoxy resin composition. Then the composition was compression molded at a pressure of 200 kg/cm$^2$ and a temperature of 170° C. for 5 minutes to give a molded article having a predetermined shape followed by heating the molded article at 175° C. for 4.5 hours in an oven to give an epoxy resin hardened product. The glass transition temperature of the product was 192° C.

Incidentally, properties of the epoxy resin hardened product was evaluated in the following manner.

Glass Transition Temperature (°C.): This was determined by obtaining a knee appearing on the temperature-linear expansion coefficient curve determined by TMA apparatus available from Rigaku Denki K.K. and the glass transition point was expressed in terms of the temperature at which the knee appeared. The measurement was performed within a temperature range of from ordinary temperature to 250° C. at a heating rate of 2° C./min.

COMPARATIVE EXAMPLE 2

The same procedures used in Example 14 were repeated except that 30 parts by weight of a polyphenol prepared by the same method used in Comparative Example 1 were substituted for 30 parts by weight of the TKXE used in Example 14, to give an epoxy resin hardened product. The glass transition point of the product was found to be 173° C.

EXAMPLE 15

TKXE (25.5 g) prepared by the same manner used in Example 2 and epichlorohydrin (55.0 g) were mixed and maintained at 100° C. Then 19 q of a 50% by weight aqueous NaOH solution was dropwise added to the mixture over 3 hours and the mixture was further ripened at 100° C. for 2 hours. After neutralizinq it with hydrochloric acid, it was washed twice with water. Then the epichlorohydrin was removed by heating at 50° C. and 40 mmHg, followed by drying at 160° C. and 7 mmHg to give 28.4 g of a desired epoxy resin. The epoxy equivalent thereof was found to be 263 g/eq.

Then there were mixed 100 parts by weight of the resulting epoxy resin, 30 parts by weight of TKXE obtained in the same manner used in Example 2 and 0.5 part by weight of 2-ethyl-4-methylimidazole. An epoxy resin hardened product was prepared in the same manner used in Example 14 using the resulting mixture. Properties of the resulting product were determined in the same manner used in Example 14.

The glass transition point thereof was found to be 202° C.

COMPARATIVE EXAMPLE 3

The same procedures used in Example 15 were repeated except that a polyphenol prepared by the same method used in Comparative Example 1 were substituted for the TKXE used in Example 15, to give an epoxy resin hardened product. The glass transition point of the product was 182° C.

We claim:

1. A method for preparing 1,1,2,2-tetrakis(4-hydroxy-3,5-dimethylphenyl)ethane comprising subjecting two molecules of bis(3,5-dimethyl-4-hydroxyphenyl)methane to dehydration-condensation under oxidizing conditions.

2. The method of claim 1 wherein the dehydration-condensation is carried out at a temperature ranging from room temperature to 310° C.

3. The method of claim 1 wherein the dehydration-condensation is carried out at a temperature ranging from 180° to 300° C. in the absence of a catalyst while blowing an oxygen-containing gas through bis(3,5-dimethyl-4-hydroxyphenyl)methane in the molten state.

4. The method of claim 3 wherein after the dehydration-condensation reaction, the resulting reaction mixture is filtered at the reaction temperature to recover crystals of 1,1,2,2-tetrakis(4-hydroxy-3,5-dimethylphenyl)ethane.

5. The method of claim 1 wherein the dehydration-condensation is carried out by dissolving bis(3,5-dimethyl-4-hydroxyphenyl)methane and an oxidizing catalyst in a solvent to form a solution and then blowing an oxygen-containing gas through the solution at a temperature ranging from room temperature to 150° C.

6. The method of claim 5 wherein the oxidizing catalyst is vanadium tetrachloride.

7. The method of claim 1 wherein after the dehydration-condensation reaction, 1,1,2,2-tetrakis(4-hydroxy-3,5-dimethylphenyl)ethane is recovered from the reaction mixture and then it is washed with a solvent.

* * * * *